US00PP14273P29

(12) United States Plant Patent

Hanes

(10) Patent No.: US PP14,273 P2
(45) Date of Patent: Nov. 4, 2003

(54) PETUNIA PLANT NAMED 'JAM WHITE'

(50) Latin Name: *Petunia hybrida*
Varietal Denomination: Jam White

(75) Inventor: Mitchell Eugene Hanes, Morgan Hill, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/389,101

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by light green-white colored flowers, compact habit and good basal branching.

1 Drawing Sheet

Genus and species: Petunia hybrida.
Variety denomination: 'Jam White'.

BACKGROUND OF THE NEW PLANT

The present invention comprises a new and distinct cultivar of petunia, botanically known as Petunia hybrida, and hereinafter referred to by the cultivar name 'Jam White'. The new cultivar is asexually reproduced from vegetative cuttings and tissue culture resulting from the cross of the seed/pod parent 00-585-1, a single white proprietary line that is unnamed and unpatented×00-233-2, a single white proprietary line that is unnamed and unpatented.

'Jam White' is a product of a planned breeding program intended to create new petunia plants with a little lighter green-white colored flowers, compact habit, good basal branching and moderately vigorous growth.

The new cultivar was created in 2001 in Gilroy, Calif. and has been asexually reproduced repeatedly by vegetative cuttings and tissue culture in Gilroy, Calif., Andijk, The Netherlands, and Guatemala over a two-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Jam White'. The data, which defines these characteristics, were collected from asexual reproductions carried out in Gilroy, Calif. The plant history was taken on 4 month old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 20 cm.
Width: Approximately 45–55 cm including flowers.
Time to produce a finished flowering plant: 9–11 weeks.
Outdoor plant performance: Full sun, free-flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 4.7–5.0 cm.
Width: 3.2–3.5 cm.
Leaf blade shape: Ovate/Elliptic.
Leaf margin: Entire.
Apex aspect: Acute.
Base aspect: Acuminate.
Leaf color: Upper side: RHS 137B (green); Underside: RHS 138A (green).
Texture: Short glandular hairs.
Venation: Palmate.
Venation color: RHS 144B (yellow-green).
Petiole length: 0.3–0.5 cm.
Petiole width: 0.2 cm.
Petiole color: RHS 144B (yellow-green).
Petiole texture: Short glandular hairs.

THE STEM

Length: 35–45 cm.
Diameter: 0.2 cm.
Internode length: 2.0–5.0 cm.
Color: RHS 144A (yellow-green).
Texture: much glandular hair of various sizes.
Stem anthocyanin: None.
Peduncle color: RHS 144A (yellow-green).
Peduncle length: 3.5–4.7 cm.
Peduncle diameter: 0.1–0.15 cm.
Peduncle texture: Many glandular hairs of various sizes.

THE BUD

Shape: Oblong.
Diameter: 0.5 cm.
Length: 2.0–4.3 cm.
Color at tight bud: RHS 1C (green-yellow).

THE FLOWER

Blooming habit: Continuous all through the growing season. Good floriferousness.
Inflorescence type: Flowers solitary in upper leaf axis.
Young flower color: White.
Young flower floret diameter: 4.5–5.5 cm.
Mature flower color: Front side, white, more white than 155D, with mid veining weak, and fading at the margins of RHS 144C (yellow-green) Underside, white.
Corolla tube color inside: RHS 151C (yellow-green) base color; RHS 151B (yellow-green) and RHS 162D (greyed-yellow) weak to moderate veining.
Corolla tube length: 2.4–2.8 cm (calyx to the petal flare).
Corolla outside texture: Glandular hairs of various sizes.
Floret form and number of petals: Funnel form, 5 lobed petals (single type) fused at base.
Flower (limb) diameter: 5.7–6.0 cm.
Petal apex shape: Retuse.
Petal margin: Entire.
Petal lobation: Moderate.
Petal waviness (ruffle of petals): very weak to none.
Petal texture: Papillose.
Calyx: 5 deeply lobed sepals, fused at base.
Sepal color: RHS 137B (green).
Sepal length: 1.1–1.5 cm.
Sepal width: 0.2–0.3 cm.
Sepal shape: Oblong.
Sepal apex: Obtuse.
Sepal texture: Long glandular hairs.
Lastingness of individual blooms: 4–8 days.
Fragrance: None observed.

THE REPRODUCTIVE ORGANS

Stamens: Five, 2 taller and 3 shorter.
Filament color: RHS 145D (yellow-green).
Pollen color: RHS 8B (yellow).
Pistil: One.
Stigma: RHS 144A (yellow-green).
Style color: RHS 145C (yellow-green).
Fruit seed set: Not observed.

DISEASE AND INSECT RESISTANCE

Not observed.

COMPARISON WITH KNOWN CULTIVARS

Compared to its female parent 00-585-1 in the following ways: The female parent is later to flower on a less vigorous plant and it has a lighter green colored leaf than does the hybrid.

Compared to its male parent 00-233-2 in the following ways: The male parent grows more upright than the hybrid. The flower on the male parent is white with a green tint in the throat of the flower while the hybrid is white with a yellow tint in the throat of the flower.

I claim:

1. A new and distinct petunia plant as shown and described herein.

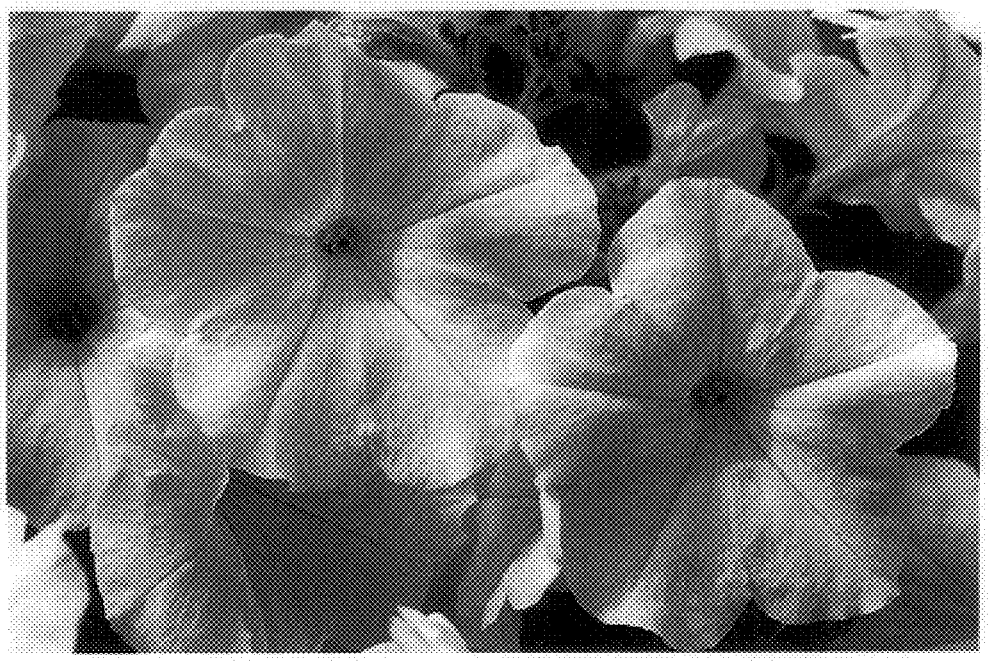

* * * * *